(12) United States Patent
MacGibbon et al.

(10) Patent No.: US 7,002,675 B2
(45) Date of Patent: Feb. 21, 2006

(54) METHOD AND APPARATUS FOR LOCATING/SIZING CONTAMINANTS ON A POLISHED PLANAR SURFACE OF A DIELECTRIC OR SEMICONDUCTOR MATERIAL

(75) Inventors: Bruce MacGibbon, Boring, OR (US); Donald F. Adamski, Portland, OR (US); Todd Stevens, Boulder, CO (US)

(73) Assignee: Synetics Solutions, Inc., Portland, OR (US)

( * ) Notice: Subject to any disclaimer, the term of this patent is extended or adjusted under 35 U.S.C. 154(b) by 364 days.

(21) Appl. No.: 10/618,446

(22) Filed: Jul. 10, 2003

(65) Prior Publication Data

US 2005/0007580 A1   Jan. 13, 2005

(51) Int. Cl.
*G01N 21/00*   (2006.01)
(52) U.S. Cl. .................... 356/237.2; 356/237.5
(58) Field of Classification Search .......... None
See application file for complete search history.

(56) References Cited

U.S. PATENT DOCUMENTS

| | | | |
|---|---|---|---|
| 4,423,331 A | 12/1983 | Koizumi et al. | |
| 4,626,101 A | 12/1986 | Ogawa et al. | |
| 4,873,430 A | 10/1989 | Juliana et al. | |
| 5,467,189 A | 11/1995 | Kreikebaum et al. | |
| 5,982,921 A | 11/1999 | Alumot et al. | |
| 6,122,047 A | 9/2000 | Stover et al. | |
| 6,191,849 B1 | 2/2001 | Maeshima et al. | |
| 6,201,601 B1 | 3/2001 | Vaez-Iravani et al. | |
| 6,215,551 B1 | 4/2001 | Nikoonahad et al. | |
| 6,707,056 B1 * | 3/2004 | Fanton et al. ......... | 250/559.44 |
| 2002/0080346 A1 * | 6/2002 | Vaez-Iravani et al. ... | 356/237.2 |
| 2002/0145732 A1 * | 10/2002 | Vaez-Iravani et al. ... | 356/237.2 |
| 2003/0156280 A1 * | 8/2003 | Reinhorn ................. | 356/237.2 |
| 2003/0210393 A1 * | 11/2003 | Vaez-Iravani et al. ... | 356/237.4 |
| 2004/0012775 A1 * | 1/2004 | Kinney et al. .......... | 356/237.2 |

FOREIGN PATENT DOCUMENTS

WO   01/80289 A1   10/2001

OTHER PUBLICATIONS

Tetsuya Kawanishi "Brewster's scattering angle and quasi-anomalous scattering in random scattering from dielectric interfaces" Opical Society of America, vol. 16, No. 2, Feb. 1999.*

* cited by examiner

*Primary Examiner*—Michael P. Stafira
(74) *Attorney, Agent, or Firm*—Marger Johnson & McCollom, P.C.

(57) ABSTRACT

To locate/size contaminants at the surface of a dielectric or semiconductor material, a P-polarized beam of light from a monochromatic solid-state source is disposed specifically at Brewster's angle and focused to form an illuminated quasi-elliptical spot on the surface that produces effectively no reflected or scattered light from the surface. The spot is scanned over the entire surface so as to assure multiple passes of any contaminant through the spot. On each pass through the spot a contaminant will produce scattered light. A novel high numerical aperture reflective or refractive system is disposed above the surface to always view the spot and to collect/redirect the bulk of the contaminant scattered light to a detector. Illumination at Brewster's angle combined with the high numerical aperture scattered light collector/redirector maximizes the signal-to-noise ratio from the detector. These core components are packaged with support subsystems as a uniquely compact and portable apparatus.

83 Claims, 11 Drawing Sheets

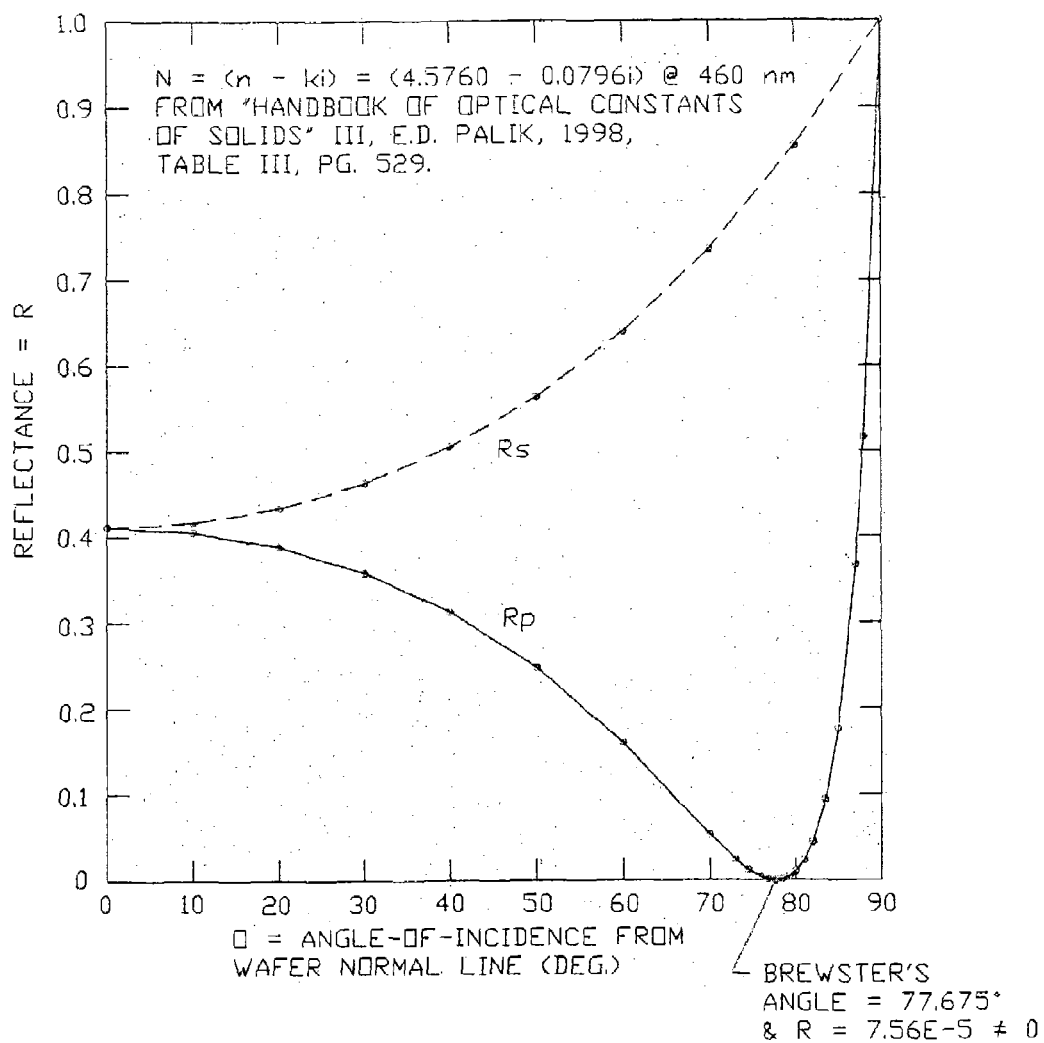
FIG. 8
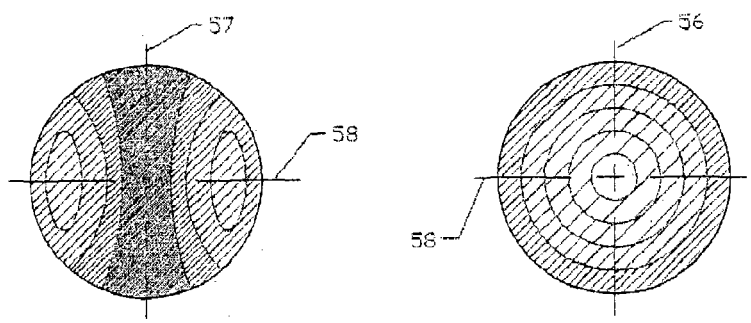
FIG. 9B  FIG. 9A

METHOD AND APPARATUS FOR LOCATING/SIZING CONTAMINANTS ON A POLISHED PLANAR SURFACE OF A DIELECTRIC OR SEMICONDUCTOR MATERIAL

BACKGROUND OF THE INVENTION

This invention relates generally to a method for inspecting a bare highly polished planar surface of a dielectric or semiconductor material for contaminants thereon.

In manufacturing semiconductor devices, multiple identical microcircuits are formed on bare highly polished planar semiconductor (silicon) wafers using a variety of sophisticated automated equipment (tools, machines). Critically essential to this manufacturing process is a requirement that the wafers are free of contaminants on or at their surface (e.g.: particles, scratches, etc.). To this end, the semiconductor manufacturing equipment is specifically designed, tested, and assembled in clean rooms prior to shipment to minimize all sources that could contaminate a wafer surface during use of the equipment. Additionally, upon arrival at the semiconductor fabrication facility the equipment is installed in large clean room areas that are also stringently controlled to minimize the possibility of wafer contamination, especially from airborne particles.

Many microcircuit chips are produced per wafer. Particle deposition on a wafer is a major cause of non-functional chips. A particle on a wafer surface can cause (1) an electrical "open" or "shorted" circuit, depending on its location relative to the electrical conductors or (2) damage to the chip as a result of chemical reactions surrounding the particle. The reduction of particle generating materials and sources in the manufacturing equipment and fabrication facility reduces wafer surface contamination, thereby improving the yield per wafer. The yield or percentage of "good" chips is the ratio of functional chips at the end of manufacturing to the total number of potential chips that could be produced from a wafer. The chip or die yield can range from 40% to 90%, depending on the maturity of the manufacturing process. As the microcircuit line widths formed on a wafer become smaller, the critical or "killer" defect size also decreases. The "killer" defect size is currently considered to be $\frac{1}{10}^{th}$ the size of the smallest line width on a microcircuit.

At key points and times during the microcircuit fabrication process, test wafers are cycled through a manufacturing tool and inspected to determine the average number of particles added to a wafer as it passes through the manufacturing tool. The inspection results are expressed in particles per wafer pass (PWP) or in particles/$cm^2$/pass. The test wafers are typically bare silicon and referred to as monitor wafers. PWP testing is well known in the semiconductor industry and is defined by SEMI (Semiconductor Equipment and Material Industry) standards.

It is necessary to reliably determine the size of contaminants so that pass/fail criterion can be applied to the PWP test results. For example, a criterion could be that the manufacturing tool is clean if $\leq 2$ particles of size $\leq 0.10$ micron were added to a test wafer. In the event the criterion is exceeded, the manufacturing tool is taken out of production. Many additional runs of test wafers through the manufacturing tool are usually required to determine the source of the contamination.

If contaminants are added to a test wafer during a PWP test, it is also important to determine their material and other characteristics to more quickly identify and eliminate their source. Typically, the test wafer is transferred to an off-production-line Scanning Electron Microscope-Energy Dispersive X-ray (SEM-EDX) for material analysis. Because of the high magnification of this instrument, searching for sub-micron contaminants can be time consuming. Therefore, the contaminant coordinates, relative to a known datum on the wafer (e.g.: the wafer notch), must be accurately mapped by the wafer inspection tool.

Though many apparatus and methods for locating/sizing contaminants on wafers have been revealed in the prior art (e.g.: U.S. Pat. No. 6,215,551 [Nikoonahad, et al.] and U.S. Pat. No. 6,122,047 [Stover, et al.], etc.) it is thought that drawbacks exist. Chief among the drawbacks is the fact that existing wafer scanning tools, based on the prior art, are located and used off-the-process line due primarily to size, weight, and lack of portability (sensitivity to movement). This requires that the PWP test wafer be (1) transported to the wafer scanning tool for a pre-scan, (2) transported to a manufacturing tool, (3) run through the manufacturing tool/robot, (4) transported back to the wafer scanning tool for a post-scan, and possibly (5) transported to the SEM-EDX if the wafer does not pass the post-scan. Typically transporting of the wafer is done in a protective transport container known in the semiconductor industry as a FOUP (Front Opening Unified Pod) for 300 mm wafers or a SMIF (Standard Mechanical Interface) pod for 200 mm wafers. The cumulative transport time delays identifying and correcting contamination problems in the manufacturing equipment and decreases production time. Other perceived drawbacks to existing wafer scanning tools include complexity (number of parts), large footprint, and high cost.

Accordingly, the need exists for a compact and portable contaminant locating/sizing method and apparatus that overcomes these perceived drawbacks in wafer scanning tools based on the prior art.

SUMMARY OF THE INVENTION

The broad concept involves directing a highly focused coherent beam of monochromatic P-polarized light to the bare highly polished planar surface of a dielectric or a semiconductor (e.g.: silicon) wafer on which surface contaminants may be present, and correlating the amount of light scattered from each contaminant with its physical size. A laser beam is P-polarized when its electric field vector is in the plane formed by the beam and its normal to the surface. Part of the incident light beam will be quasi-hemispherically scattered from a contaminant, part may be externally reflected from the wafer surface, and part will be internally reflected (absorbed) into the wafer surface. In general, more light will be scattered from larger contaminants depending on their shape and material (i.e.: complex refractive index). The magnitude of the external and internal reflections at the wafer surface is dependent on the complex refractive index of the wafer material, the angle-of-incidence of the light beam on the surface, and the polarization state of the light beam. These optical phenomena were discovered, mathematically defined, and published by Fresnel, Rayleigh, Brewster, Maxwell, and Stokes and their work is well known to persons skilled in optics.

The present invention is not really concerned with classifying the surface contaminants as particles, scratches, crystal-originated pits (COPs), other pits, dimples, etc. or identifying their material which may require specific (and possibly a multiplicity of) light sources and detector orientations, polarizations, etc. as suggested in the prior art. Rather, the present invention is aimed at describing a comparatively simple, compact and portable apparatus and method to locate/size surface contaminants on a bare dielectric or semiconductor material.

Two possible uses include an apparatus and method for locating micron and sub-micron size contaminants at a surface of (1) bare silicon (a semiconductor) wafers used in microcircuit manufacturing and (2) quartz (a dielectric) plates used to make masks for microcircuit lithography. The silicon wafer application involving one and two light sources are used herein to describe the method and apparatus.

The primary element of such a surface contaminant location/sizing apparatus is a scanning module preferably comprised of the following elements: (1) a vacuum chuck for holding a wafer as it is inspected; (2) a small coherent light source that produces a narrow monochromatic P-polarized beam of light (i.e.: solid state thermoelectrically cooled laser); (3) light beam conditioning optics that produce a diffraction limited beam that has a circular cross-section with a Gaussian irradiance profile centered about the optical axis and is focused to a fine circular spot centered at a point on the optical axis that can be disposed to lie in the plane of the wafer so as to produce a quasi-elliptical illuminated spot on the wafer surface; (4) a means to direct the optical axis of the light beam to the wafer surface specifically at Brewster's angle (i.e.: the angle of minimum reflectance for P-polarized light—also called the "principal angle of reflectance" for semiconductors and metals); (5) a high numerical aperture light collector (e.g.: a highly elongate ellipsoidal reflector or a refractive lens system) positioned above the wafer surface and focused on the center of the illuminated spot on the wafer surface to collect the bulk of the quasi-hemispherically scattered light from the contaminant and direct it to a light detector; (6) an optional detector/beam dump interposed to intercept, measure, and dissipate very low level light reflected from the wafer surface opposite the incident light beam; (7) a detector to sense the wafer notch to establish a datum on the wafer surface; (8) a low dark noise and ultra fast/sensitive electro-optical detector (e.g.: a photomultiplier tube [PMT] or alternately a solid state photodiode) for measuring the intensity of the scattered light collected; (9) a means of moving the wafer surface and the integrated laser, scattered light collector/detector, and an optional beam dump assembly relative to each other such that all areas of a wafer surface can be mapped in a reasonable time period (<3 min. for a 300 mm wafer); and (10) control and power distribution electronics. Additional system elements, not discussed herein, but known in the art, include a means to keep the light beam focal point in the wafer plane regardless of wafer tolerances (thickness, flatness, etc.) and a means to dampen deleterious vibrations in the system. All of these scanning module elements are enclosed in a clean and sealable module with a door to allow a wafer to be inserted and removed by a robot. The robot is not part of the apparatus.

Remote from the scanning module is a second module housing a primary power supply and distribution elements, a vacuum source, and a processing unit for (1) analyzing the detector electrical output signals and comparing them to a calibration curve relating signal magnitude to particle size, and (2) coordinating the timing associated with the motion of the wafer relative to the scattered light collector/detector so that the defect size and location on the wafer surface can be determined and plotted (mapped).

The high numerical aperture scattered light collector maximizes the capture of the scattered light from a contaminant. This coupled with illumination at Brewster's angle, which minimizes specular reflection of incident light from the wafer surface, maximizes the signal-to-noise ratio. This combination of items has not been exploited in the prior art dealing with wafer scanning apparatuses. The prime sources of noise in the system are scatter from sub-micron surface roughness (haze) on the wafer surface and detector dark current. The combination of these is small and relatively constant.

Contaminant detection resolution down to about 0.05 $\mu$m should be possible with this invention.

The foregoing and other objects, features, and advantages of the invention will become more readily apparent from the following detailed description of a preferred embodiment of the invention that proceeds with reference to the accompanying drawings.

BRIEF DESCRIPTION OF THE DRAWINGS

FIG. 8 is a graph of reflectance vs. angle-of-incidence for P and S-polarized 460 nm light beams and Brewster's (principal) angle on a bare highly polished planar silicon surface.

FIGS. 9A and 9B illustrate how the incident and reflected laser beam cross-sections look on a flat screen inserted in the beams perpendicular to the beam optical axis.

DETAILED DESCRIPTION

Figure 1:
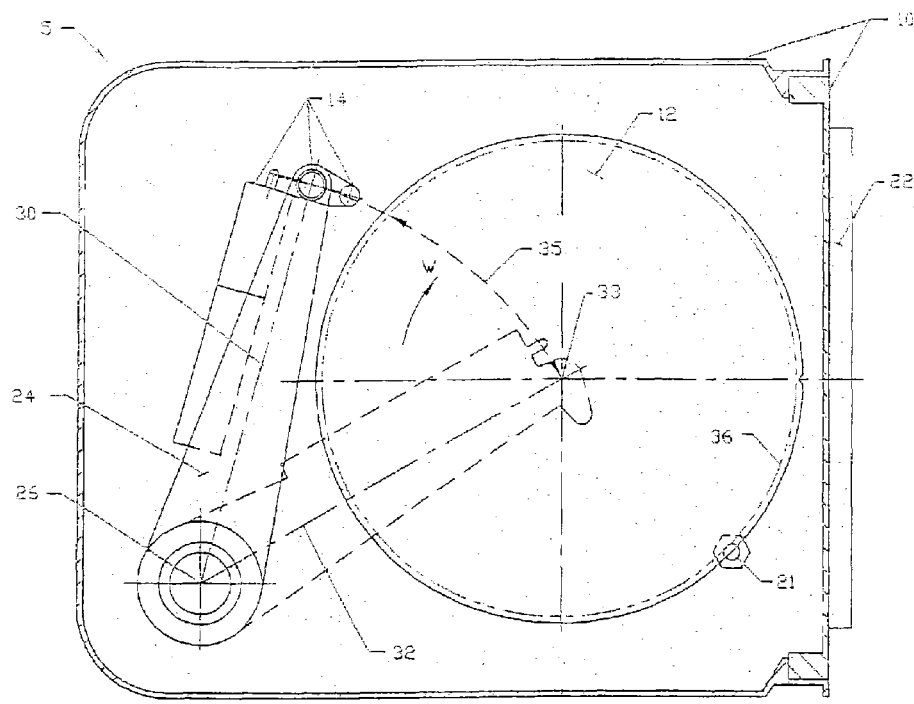
FIG. 1 shows a top view of the apparatus, constructed according to a preferred embodiment of the invention, with a pivoting arm that moves the instrument group over the surface of a wafer to be scanned and a light source wavelength in the range $\leq$470 nm.
Figure 2:
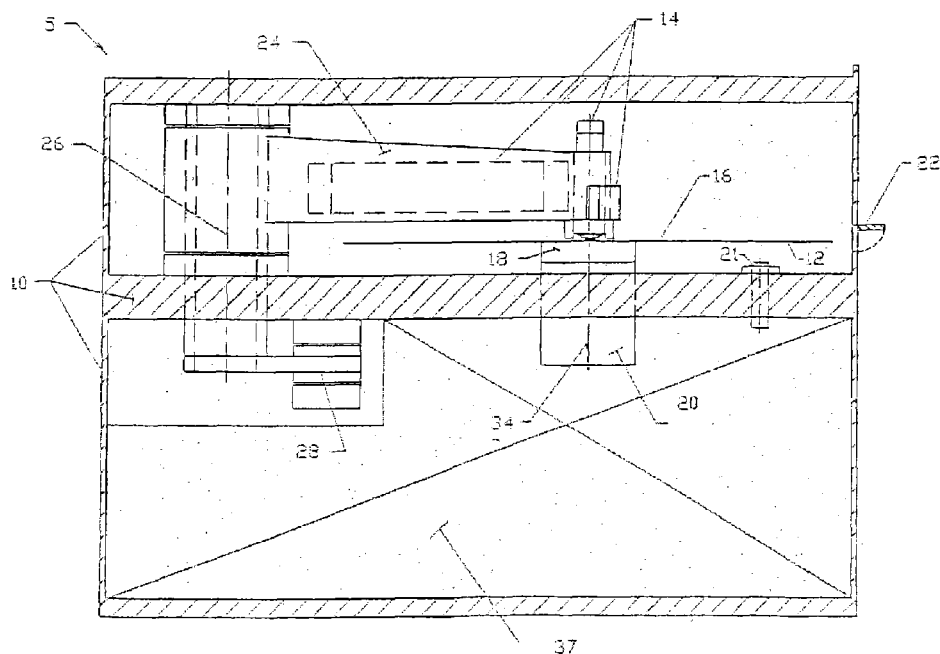
FIG. 2 shows a side view of the FIG. 1 apparatus with the light source positioned at the stop scan point directly over the spin axis of the wafer.

As illustrated in FIGS. 1 and 2, the apparatus embodying the invention is a compact portable scanning module 5 comprised of an air-tight enclosure 10 housing wafer 12 and instrument group 14 used to detect contaminants on the top surface 16 of wafer 12. Instrument group 14 is comprised of a physically small laser, laser beam conditioning optics, scattered light collector/detector, and an optional reflected beam detector/dump. Enclosure 10 is the same size as a standard 25 unit 300 mm wafer FOUP (Front Opening Unified Pod) except that it may be up to 4 inches longer (see FIG. 7A). It is configured to lock and seal to a standard 300 mm loadport in the conventional manner. Wafer 12 is mounted on a vacuum chuck 18 integral with an ultra-low-vibration and precise speed-controlled electric spindle motor/encoder/vacuum-line assembly 20. Thus, wafer 12, vacuum chuck 18, and assembly 20 all rotate about axis 34. Detector 21 senses the wafer notch to provide a datum on the wafer surface. Wafer 12 is inserted, centered, and placed on vacuum chuck 18 through an elongate door 22 by a robotic arm (not shown) that may or may not be part of the overall system. A pivoting arm 24 is fixed at pivot axis 26 and is precisely moved by a second ultra-low-vibration and speed-controlled electric motor 28. Axes 26 and 34 are parallel. Instrument group 14 is mounted at the free end of arm 24 and is moved, at a constant stand-off distance, in an arc over the top surface 16 of wafer 12 between an initial park position 30 and a second position 32. As defined later herein, instrument group 14 projects a focused laser beam to produce an illuminated spot on the top surface 16 of wafer 12. Arc 35 is the path of the center of the laser beam illuminated spot on wafer top surface 16. The arm park position 30 places the pivoting arm 24 entirely outside the periphery of wafer 12 so that it does not restrict motion of the robotic arm/end-effector (not shown) as it positions the wafer 12 on vacuum chuck 18. The arm second position 32 places the laser beam illuminated spot center at stop scan point 33, which is directly over the wafer 12 center-of-rotation. The motion of pivoting arm 24 allows the entire surface of rotating wafer 12 to be scanned in a spiral pattern as instrument group 14 moves from a start scan circle 36 to the end scan point 33. Circle 36 is the inner peripheral boundary of the SEMI standard edge exclusion area on the wafer. While arm 24 moves from the park position 30 to start scan circle 36 the laser beam is blocked by a shutter and no data is acquired. The shutter also blocks the laser beam as pivoting arm 24 returns from position 32 to position 30. Electronics elements (not shown) housed in the lower portion 37 of enclosure 10 (1) control and accurately time the relative movements of arm 24 and wafer 12 to identify the precise point on wafer 12 under inspection by the instrument group 14 at any moment of time, (2) control the laser and its beam shutter, (3) control the detector, and (4) route detector signals to the processing electronics.

The pivot arm 24 and center shelf of enclosure 10 incorporate a passive or active means to damp vibration (internal and external to the apparatus) while the top half of enclosure 10 incorporate means to damp air turbulence caused by the rotating wafer surface drag. All such means are known to those skilled in the art of vibration control.

Figure 3:
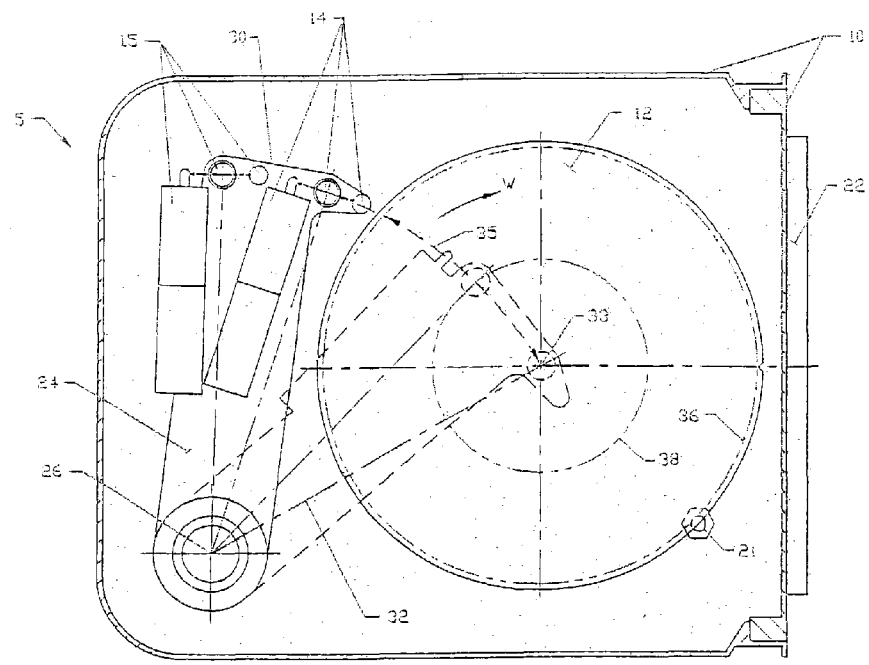
FIG. 3 shows a top view of an alternate embodiment of the FIG. 1 apparatus with two identical instrument groups arranged to reduce the scan time by a factor of two.

FIG. 3 illustrates a second embodiment of scanning module 5 in which the time to scan a wafer is halved by modifying pivot arm 24 to accommodate a second instrument group 15, identical to and spaced from instrument group 14 by a distance approximately equal to half the wafer radius along arc 35. All other elements of scanning module 5 are otherwise unchanged. Instrument group 14 thus scans from a new start scan circle 38 to stop scan point 33 while instrument group 15 simultaneously scans from start scan circle 36 to a stop scan circle that is essentially the same as start scan circle 38 for instrument group 14 (in practice there is a small overlap of these start and stop scan circles). Start scan circle 38 has half the radius of start scan circle 36.

Figure 4:
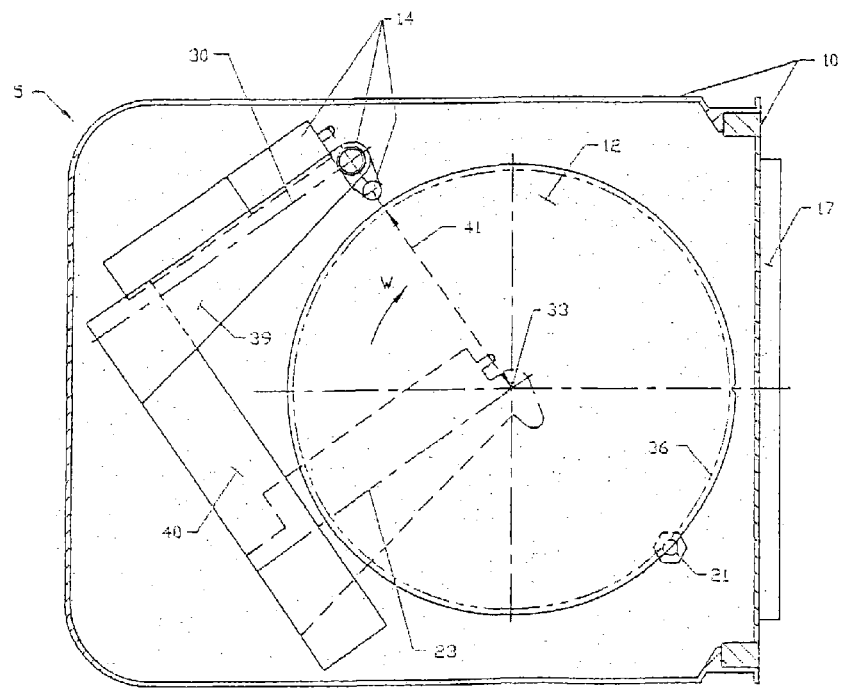
FIG. 4 shows a top view of an alternate embodiment of the FIG. 1 apparatus with a linear motion arm for the instrument group vs. the pivoting arm shown in FIGS. 1 through 3.

A third embodiment of scanning module 5 is illustrated in FIG. 4 wherein pivoting arm 24 is replaced by a cantilever arm 39 attached to a linear stage 40 to move instrument group 14 so that its projected laser beam illuminated spot follows a linear path 41 on wafer top surface 16. All other elements of scanning module 5 are otherwise unchanged.

It follows that the dual instrument group concept of FIG. 3, used to halve the scan time, can be extrapolated to include more than two instrument groups disposed on a suitable pivot arm (ala FIG. 3) or cantilever arm (ala FIG. 4) where the scan time reduction factor is the member of instrument groups employed.

Figure 5:
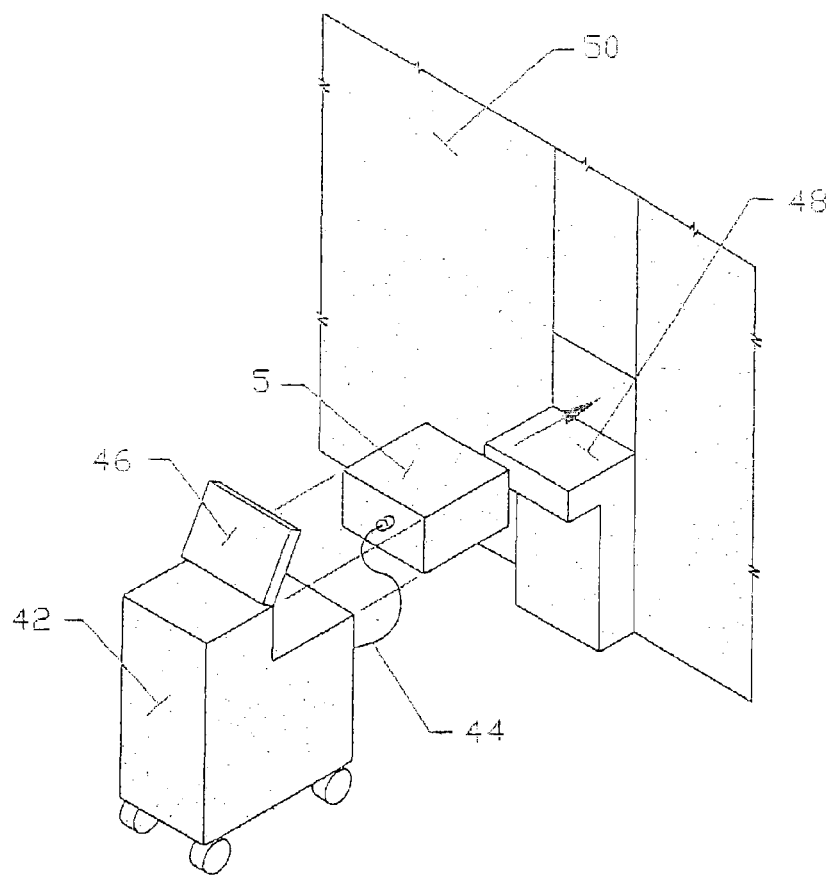
FIG. 5 shows a pictorial view of the apparatus overall system as a compact portable and self-contained unit.

Irrespective of the scanning module 5 internal configuration the overall compact and portable system data processing electronics/computers, power supplies/distribution, vacuum source, and touch screen control/display are located outside of scanning module 5 as conceptually illustrated in FIG. 5. Therein the overall system is comprised of scanning module 5 interconnected to a support cart 42 by detachable umbilical 44. Support cart 42, not further discussed herein, is a manually pushed portable unit that houses the electronics, power supplies, and vacuum source in its lower part and a touch screen control/display 46 that folds into the top of cart 42. Umbilical 44 is comprised of control, data, power, and vacuum lines. Power for the components in cart 42 may by supplied by on-board rechargeable batteries or it may be plugged into a wafer fabrication facility wall power outlet. The novel element of the system is the scanning module 5 that is stored on the rear top portion of support cart 42 when not in use. To be used, scanning module 5 is removed from support cart 42 and docked into any of many existing standard FOUP loadports 48 mounted in the walls 50 of the wafer fabrication facility process cells.

Figure 6:
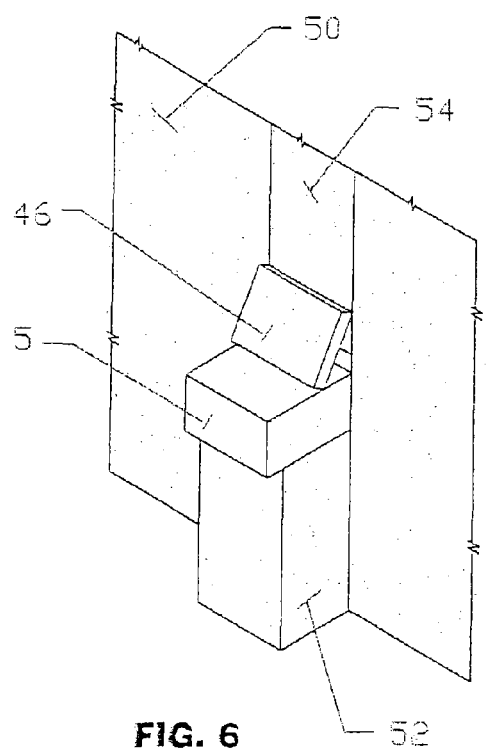
FIG. 6 shows a pictorial view of the apparatus overall system as a compact system hard mounted (not portable) on a standard loadport size wall panel.

FIG. 6 shows an alternate non-portable embodiment of the overall scanning system wherein cart 42 and its rechargeable batteries are eliminated. The remaining elements are integrated onto a support compartment 52 that is integrated underneath scanning module 5 and touch screen control/display 46 onto a standard sized loadport panel 54. This assembly is connected to the wafer fabrication facility electric power and vacuum supplies.

The preferred coherent monochromatic light source is a laser that (1) is small ($\leq$[5 in. L×3 in. W×1.25 in. H]), (2) is light-weight ($\leq$0.5 lb.), (3) is solid-state (no gas plasma involved), (4) is thermoelectrically cooled, (5) operates only in a continuous wave (CW) TEMoo mode at a single wavelength in the preferred ranges of ≦470 nm and ≧700 nm or the non-optimum range of >400 nm to <700 nm, (6) has a mode quality $M^2 \leq 1.1$, (7) has minimum integrated beam power of 25 mW for the <700 nm wavelength options, and ≧200 mW for the ≧700 nm wavelength option, (8) has a capability to adjust beam power through a computer, (9) is highly wavelength and pointing stabilized, (10) has a beam polarization ratio ≧100:1, (11) can be focused (with appropriate optics) to a diffraction limited spot with a circular cross-section, a Gaussian irradiance profile centered about the optical axis, and a diameter in the range of 8 to 12 microns, and (12) can be operated at full power for at least 10,000 hours. This disclosure also covers the use of other future light sources that meet these or more stringent criteria.

Figures 7A, 7B, 7C, 7D, 7E:
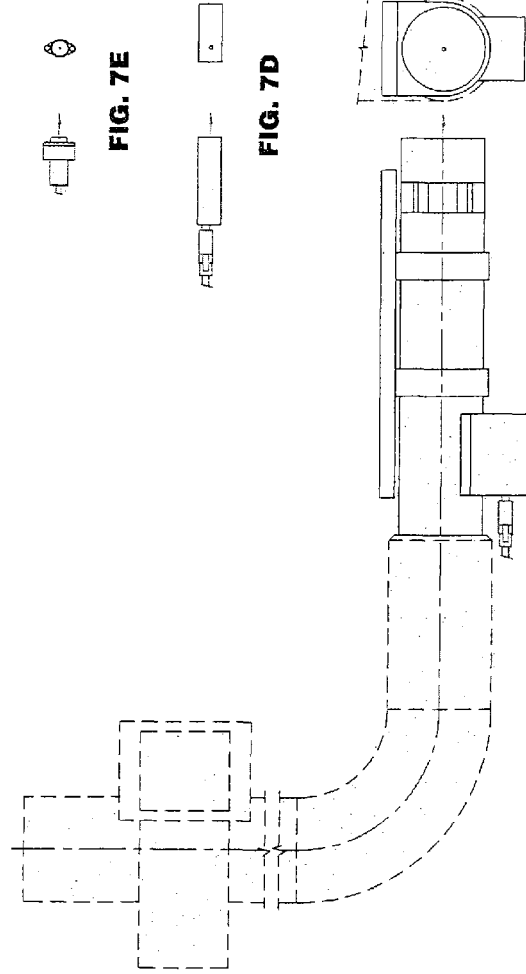
FIGS. 7A through 7E collectively show the relative size and weight of gas and solid state (no gas plasma involved) lasers, in the wavelength range of 400–1200 nm, to each other and a standard 300 mm wafer FOUP (Front Opening Unified Pod).

The impact of a small light-weight light source on the ability to produce a compact and portable scanning module 5 that is approximately the size of a standard 25 wafer 300 mm FOUP is evident in FIGS. 7A through 7E that show the relative size of a FOUP compared to state-of-the-art gas and solid state lasers. The laser bodies are shown in bold solid outlines. The requisite electrical connectors are shown in light outlines although they may also be located at the remote end of an electrical cable that is hard-wired to the laser. Requisite cooling fans and ducts are shown in dashed outlines. Control boxes are not shown since they would not be located in the FOUP size module. FIG. 7A shows the side profile of a standard FOUP with a length extension (4") denoted by dashed lines. FIG. 7B shows a 633 nm 23 mW air convection cooled Helium-Neon gas laser weighing about 3 lb. FIG. 7C shows a 488 nm 30 mW air cooled Argon-Ion gas laser with requisite cooling fan and duct all weighing about 15 lb. FIG. 7D shows a 405 nm or 488 nm 25–50 mW thermoelectrically cooled solid state lasers that weighs about 0.5 lb. FIG. 7E shows a 830 nm thermoelectrically cooled solid state laser (<200 mW) that weighs about 0.25 lb. Note that gas lasers are generally run at less than full beam power output (≈25% less) to increase service life. The gas lasers of FIGS. 7B and 7C are of the type currently used in some existing wafer scanners and are clearly not suitable for this invention due to size and weight.

For each laser (wavelength) used, a calibration curve is determined so that contaminant size can be correlated with the measured intensity of the scattered light. This calibration is accomplished using a semiconductor industry accepted standardized procedure that involves scanning a calibration wafer surface that has patches of micron and/or sub-micron diameter Polystyrene Latex (PSL) spheres deposited on its surface. The PSL spheres have a smooth surface. For each size PSL sphere, a generally well-defined and repeatable scatter pattern is produced for any given laser beam wavelength, polarization, and angle-of-incidence. The sizes of the PSL spheres, their deposition procedure, and the ready-to-use PSL calibration wafer are traceable and certified through the NIST (National Institute of Standards and Technology).

However, real-world contaminants produce scatter signatures different from the well-behaved PSL spheres. Invariably, they (1) are multi-faceted vs. spherical, (2) have irregular flat and curved faces, (3) may be clumped together, and (4) are composed of a variety of materials that have different complex refractive indices (i.e.: [n–ki] where n=refractive index; k=absorption index; and i denotes imaginary component). For these reasons, at the same monochromatic illumination beam wavelength, polarization, and angle-of-incidence real-world contaminants can scatter more or less light than a certified size PSL sphere of the same actual physical size. Thus, per semiconductor industry accepted convention, the scatter signature magnitude from a contaminant is matched to that of a PSL sphere under the same illumination conditions and the PSL sphere size is reported as the contaminant size (e.g. PSL equivalent size).

Contaminants found on the polished surface of silicon wafers (defined in the open literature and summarized in U.S. Pat. No. 6,122,047, Sep. 10, 2000) and their characteristic complex refractive indices include (1) dielectrics, e.g.: PSL, $SiO_2$, and $Al_2O_3$ (small n, k=0), (2) good conductors, e.g.: silver (Ag) and copper (Cu) (small n, large k), (3) gray metals, e.g.: tungsten (W) (large n, large k), and semiconductors, e.g.: silicon (Si) particles (large n, small k). Reflectance curves vs. monochromatic light beam angle-of-incidence, similar to that for silicon illuminated at 460-nm as shown in FIG. 8 (see next paragraph), can be obtained for all these materials by those skilled in the art of optics.

The laser and its integrated beam conditioning optics are mounted relative to the wafer surface so as to direct the focused laser beam optical axis to the surface specifically at Brewster's angle (principal angle) for the specific wavelength and dielectric or semiconductor wafer and with the beam P-polarized (e.g.: electric field vector parallel to the incident plane). The wafer can be in any gas (preferably non-flammable) or vacuum ambient environment. The reflectance for a bare highly polished planar dielectric material under P-polarized light goes to zero at Brewster's angle which is different for each wavelength in accord with Fresnel's Laws of Reflectance and Brewster's Law that are well understood by those skilled in optics. For a semiconductor the reflectance under P-polarized light approaches, but does not reach a zero value. FIG. 8 illustrates this for silicon in air under P and S polarized 460 nm laser beams at various angles-of-incidence from 0° to 90° (measured from a line normal to the wafer surface). Therein, it can be seen that at an angle-of-incidence of 77.68° the P-polarized light produces nearly zero ($7.56 \times 10^{-5}$) reflectance (i.e.: effectively as if the surface were not there). Thus, conceptually, P-polarized monochromatic light incident on a highly polished dielectric or semiconductor surface at Brewster's angle will make the scatter intensity from a contaminant resting on the surface closely approach that from the same contaminant in free space under the same illumination wavelength and intensity. This phenomenon has not been exploited in the prior art dealing with wafer scanning and is a key element of this invention.

As known to those skilled in the art of laser optics, the incident laser beam has a circular cross-section with a symmetrical near Gaussian irradiance (intensity) distribution at all points along the beam optical axis. The $1/e^2$ irradiance levels of this set of near Gaussian irradiance distributions form a hyperboloidal envelope (similar to an hourglass), the longitudinal axis of which is the laser beam optical axis. The minimum diameter (Gaussian waist) of the hyperboloid lies wholly in the laser beam focal plane and is centered on the laser beam focal point. The beam thus converges to the Gaussian waist and diverges beyond it. The beam wavefront is flat in the plane of the Gaussian waist, but has curvature in all other planes.

These incident laser beam phenomena coupled with the effectively zero reflectance for a P-polarized laser beam incident on a dielectric or semiconductor bare polished surface at Brewster's angle (as defined in the above paragraph) result in a unique cross-sectional irradiance (intensity) distribution for the reflected beam. Looking from the focal point along the optical axis the incident beam appears as shown in FIG. 9A while the reflected beam appears as shown in FIG. 9B. Understand that in both these figures light intensity in inversely proportional to the density of the crosshatched areas (i.e.: darkest crosshatching represents zero light). Additionally, in reality the intensity transition from no light is a smooth gradient vs. the crosshatched contour areas used in the figure. The cross-section of FIG. 9A is a top view of a Gaussian irradiance distribution centered on and symmetrical about the beam optical axis. In FIGS. 9A and 9B the vertical axes 56 and 57 (respectively) are parallel to wafer top surface 16 (see FIG. 1) and perpendicular to the plane 58 formed by the optical axes of the incident and reflected beams. About axis 57 in FIG. 9B there is a pronounced dark (no light) central band that blends, with smooth irradiance increase, to two dim outer lobes. The ratio of integrated power (mW) for the two lobe reflected beam to that for the input laser beam is about 0.00016:1.

Figure 10B:
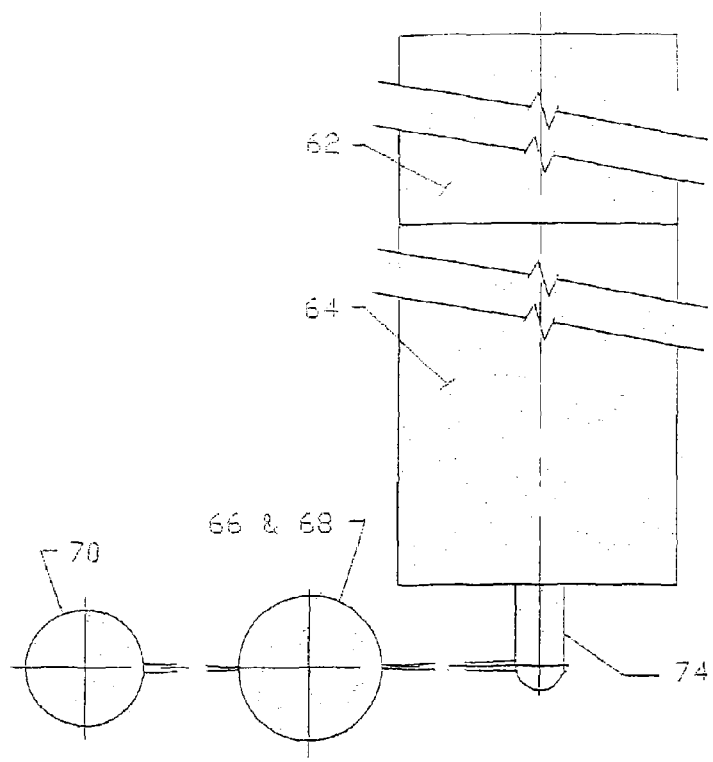
FIGS. 10A and 10B show top and front views of the component layout for the preferred instrument group for a laser in the $\leq$470 nm wavelength range.
Figure 10A:
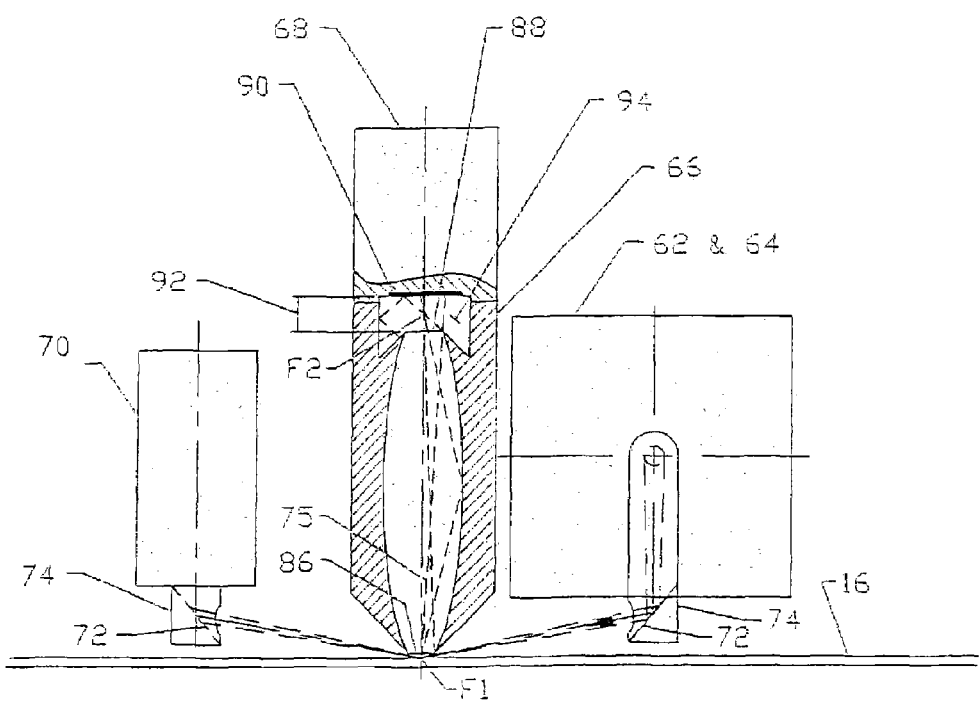

The very low intensity two lobe reflected beam phenomenon can be dissipated in an optional simple beam dump or a charge-coupled device (CCD) camera (or, alternately, an electro-optical linear or quadrant detector, etc.) beam dump 70 shown in FIGS. 10A and 10B. If a CCD camera is used the two lobe beam cross-section image on a CCD camera monitor can be used to assure that the beam is disposed at Brewster's angle (i.e.: dark band in the monitor image must be centered as shown in FIG. 9B).

FIGS. 10A and 10B in conjunction with FIGS. 1 through 4, presents top and front views (showing component relative size proportions) of instrument group 14 positioned at a constant distance just above wafer top surface 16 and configured according to a first embodiment of scanning module 5. Instrument group 14 is comprised of a laser 62 (in the $\leq$470 nm preferred wavelength range), laser beam conditioning optics 64, scattered light collector 66 (a highly elongate ellipsoidal reflector), a scattered light detector 68, and the optional reflected light beam dump/CCD camera (or other detector) 70.

The laser beam conditioning optics 64 include an electronically controlled beam shutter and produce a diffraction limited beam with a circular cross-section, a symmetrical Gaussian irradiance distribution about the optical axis, and finely focused to a circular point centered on the optical axis of the beam. The focal point on the laser beam optical axis is permanently positioned to be coincidental with the focal point F1 of the scattered light collector 66. The design of such an optics system is well known to those skilled in the art of laser optics and is not further discussed herein.

Figure 11A:
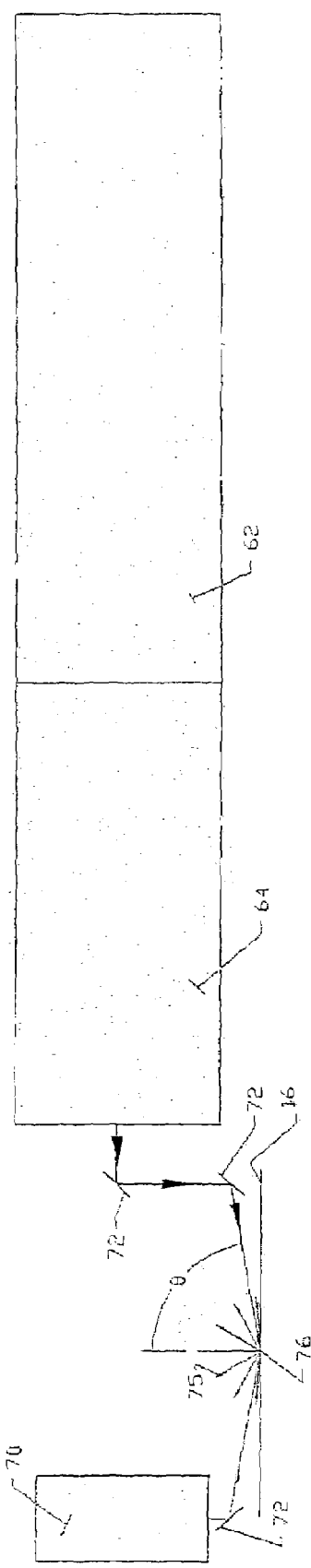
FIGS. 11A and 11B show respectively the preferred optical layout of the instrument group for lasers in the two preferred wavelength ranges of $\leq$470 nm and $\geq$700 nm.
Figure 11B:
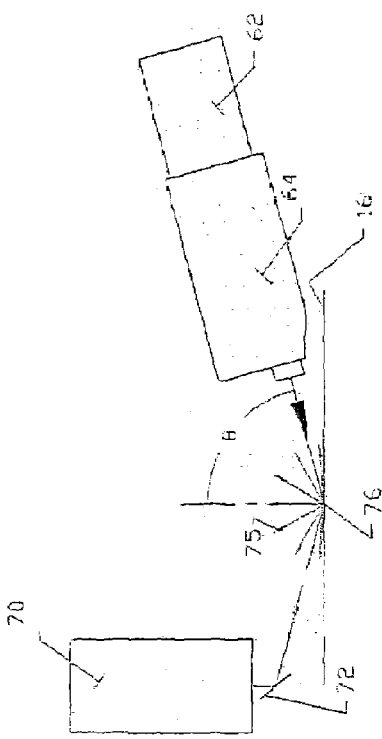

The solid state laser and reflected beam path layouts for the two preferred laser wavelength options (previously defined) are shown in FIGS. 11A and 11B. For clarity, FIG. 11A, for the $\leq$470 nm laser option, shows laser 62 and beam conditioning optics 64 rotated 90° (unfolded) from that shown in FIGS. 10A and 10B and three beam directing front surface planar mirrors 72 (not all visible in FIGS. 10A and 10B) while FIG. 10A shows beam shrouds 74 (not depicted in FIG. 11A) that appropriately position mirrors 72. FIG. 11B, for the $\geq$700 nm laser option, is planar as shown because solid state lasers in that wavelength range are significantly smaller and lighter weight than the $\leq$470 nm solid state lasers (see FIGS. 7D and 7E) and the optical beam path need not be folded. Components shown in FIGS. 11A and 11B are shown in relative size proportions.

Figure 10C:
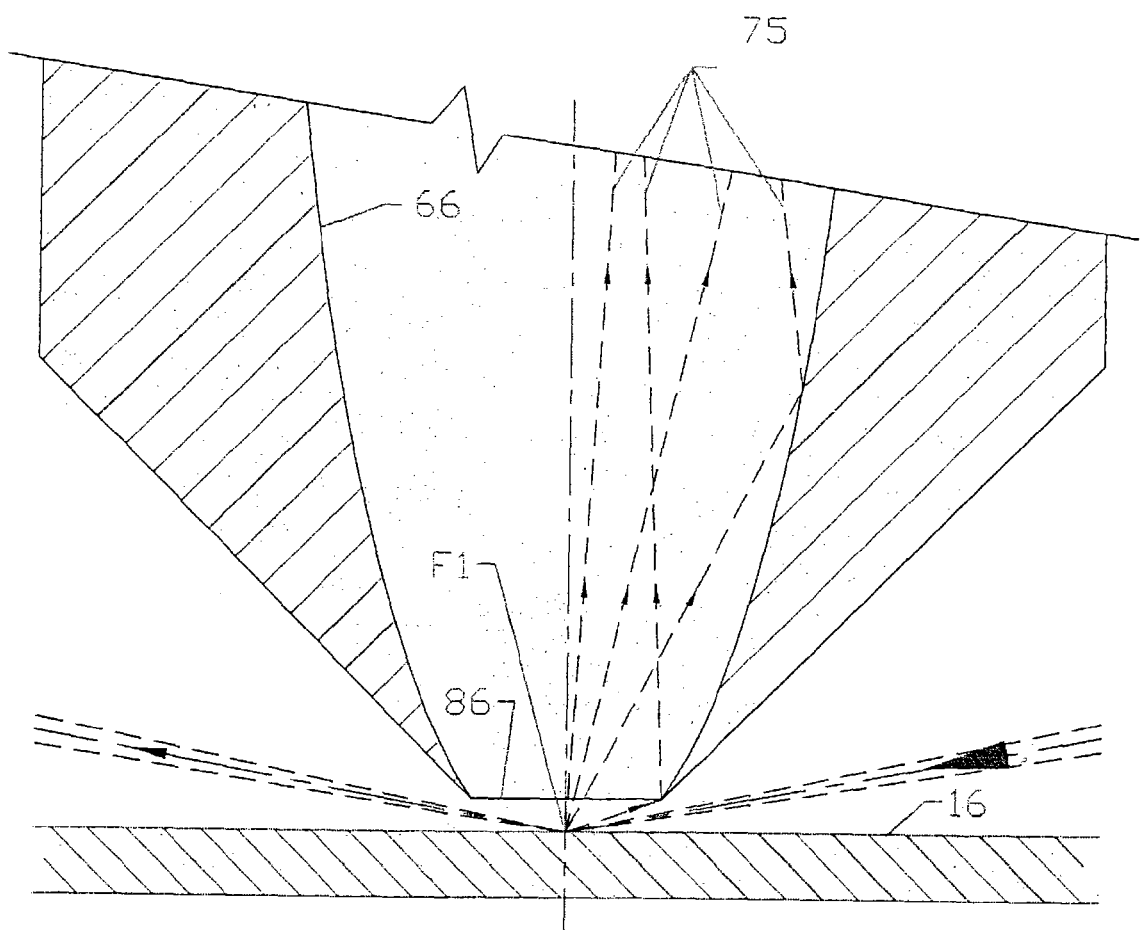
FIG. 10C, a blow-up from FIG. 10A, shows detail of the laser beam passing under the highly elongate ellipsoidal reflector.

As further depicted in FIG. 10A, the scattered light collector 66 focal point F1 (coincidental with laser beam point-of-focus) is constrained to lie in the wafer top surface plane 16 by manual or automatic means (well known to those skilled in the art and not further discussed herein) due to deflection resulting from gravity and rotational forces, warp, and variations in thickness of a wafer. The wafer thickness variations and warp are defined by industry accepted tolerances for wafers. For clarity FIG. 10C is a blow-up of the F1 end of scattered light reflector 66, the incident and reflected laser beams, and the wafer top surface 16. The incident laser beam thus forms a constant size quasi-elliptical illuminated spot 76 on the wafer top surface 16 centered on the scattered light collector 66 focal point F1. It follows that the field-of-view 78 of the scattered light reflector 66 circular entrance aperture 86 (see FIG. 10C) is also centered on point FI as depicted in FIG. 12 (items shown are not in true relative proportions).

Figure 12:
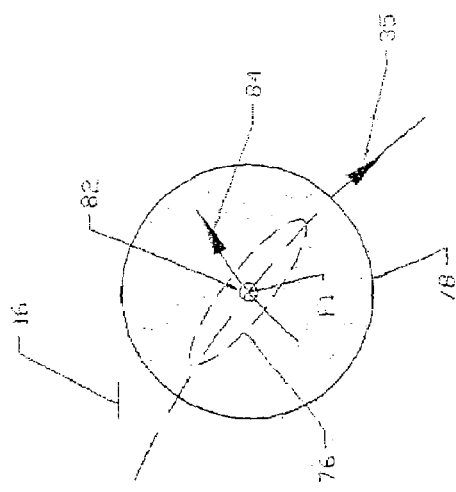
FIG. 12 shows the relationship of the illuminated spot, light collector field-of-view, pivoting arm/instrument group path, and wafer/contaminant path.

Also shown in FIG. 12, point F1 and the illuminated spot 76 (both constrained by pivoting arm 24) follow an arc path 35 (see FIGS. 1, 3, and 15) over wafer top surface 16 while the wafer rotates. In the alternate embodiment of FIG. 4 the path is a straight line 41 versus a curved path 35. Thus, as seen by detector 68 (FIG. 10A) a contaminant 82, located at any fixed radius on wafer top surface 16, will pass through illuminated spot 76 multiple times as the illuminated spot moves in arc path 35 and will scatter light 75 each time it is illuminated. However, the contaminant will not always pass through the center of the illuminated spot as depicted in FIG. 12. For a fixed laser beam power, the magnitude vs. time trace of the scattered light 75 signal from the detector 68, caused by a contaminant 82, depends on where the contaminant passes through the illuminated spot 76. The multiple scatter light traces from any given contaminant are processed by the support electronics to determine the location (relative to the datum established by detector 21—see FIG. 1) and PSL sphere equivalent size of the contaminant on the wafer top surface 16.

The first embodiment of the scattered light reflector 66 (see FIG. 10A) is a high numerical aperture (NA>0.85) highly elongate ellipsoidal reflector disposed as defined above and with its major axis perpendicular to wafer surface so as to collect effectively all of the light scatter 75 from a contaminant. The distribution of the light scatter 75 is quasi-hemispherical. Within this quasi-hemisphere the magnitude and polarization of scatter rays at different azimuth and elevation locations will vary with the size, shape, and material of the contaminant as indicated above and in the prior art. However, this is not important for this invention since the reflector/detector combination integrates effectively all of the total scattered light magnitude vs. time per contaminant pass. For the $\leq$470 nm laser, as shown in FIG. 10C the laser beam is directed under an edge of ellipsoidal reflector 66 entrance aperture plane 86 and the miniscule power (compared to the input laser beam power) reflected beam emerges out from under an opposite edge of aperture plane 86. The entrance aperture plane 86 is disposed above the first focal point F1 of the ellipsoidal reflector while the exit aperture plane 88 is located below the second focal point F2. The ratio of the major to minor axes of the ellipsoidal reflector is $\geq$4.5:1, the extent of the reflective inner surface is 90–95% of the distance between the two focal points F1 and F2, and the ellipsoid minor diameter to entrance aperture diameter ratio is less than 3.1:1. These proportions make it distinctly different from the prior art that show a half or less of an ellipsoid, paraboloid, or spherical reflector with exit aperture less than or equal to the minor axis diameter of the particular reflector shape. Thus, the novel highly elongate ellipsoidal reflector 66 of this invention can capture/redirect significantly more of the light scattered from a contaminant. This improves the signal to noise ratio of detector 68. The reflective inner surface of ellipsoidal reflector 66 is preferably highly accurate, highly polished, and optically coated (optimized for the laser wavelength).

The sensitive face 90 of detector 68 is spaced a distance 92 (see FIG. 10A) from exit aperture plane 88 so that the scattered light rays from a calibration PSL sphere at point F1 on wafer surface 16 produces a signal maximum from detector 68. A light ray dump cavity 94 is symmetrically distributed about the face of the detector 68 and ellipsoidal reflector exit aperture 88 to extinguish any scattered rays that may partially reflect off of the material covering the sensitive face 90 of detector 68. The ellipsoidal reflector assembly (comprised of elements 66, 68, and 94 in FIG. 10A) is specifically configured so that contaminant scattered rays (photons) pass only one time through the reflector to the detector sensitive surface 90. This novel arrangement makes it distinctly different from integrating sphere arrangements in the prior art.

Figure 13A:
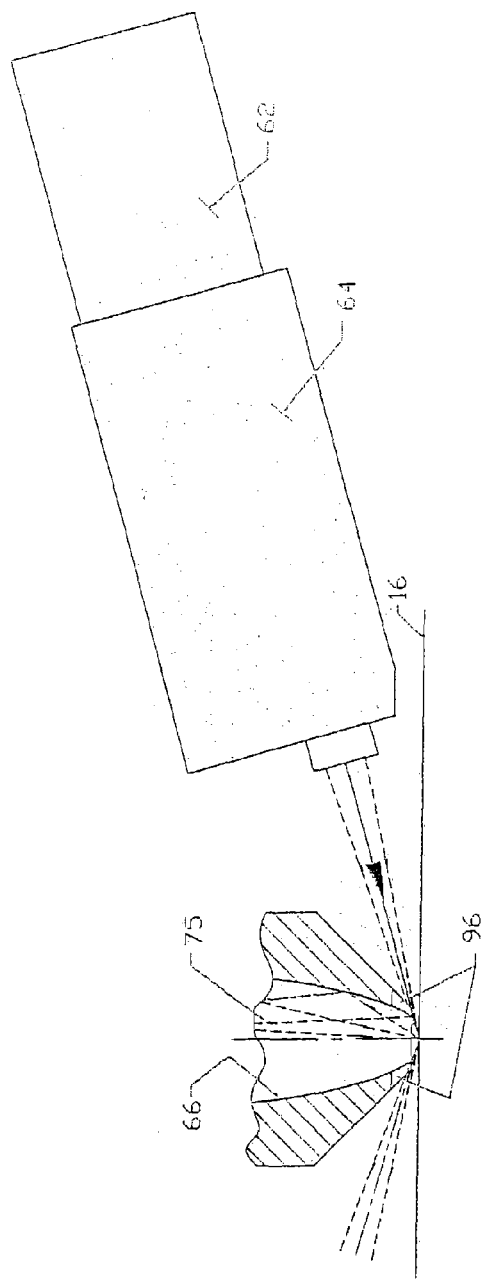
FIGS. 13A and 13B show respectively a side cross-section view and a view rotated 90° to it to illustrate a notched end variation of the highly elongate ellipsoidal reflector so it can freely pass the incident and reflected laser beams in the $\geq$700 nm range.
Figure 13B:
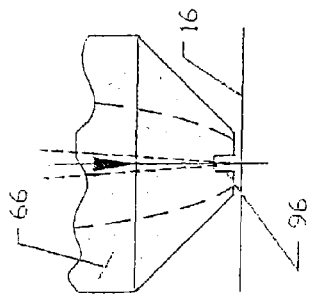

Depending on laser 62 wavelength (dictates the angle-of-incidence of the laser beam optical axis and beam cone angle) and to maintain a high numerical aperture for the ellipsoidal reflector 66, notches 96 can be cut 180° apart into the wafer side of ellipsoidal reflector 66, as depicted in FIGS. 13A and 13B. FIG. 13A shows the notched configuration in the plane of the incident and reflected laser beams. FIG. 13B shows the notch configuration perpendicular to the plane of the incident and reflected laser beams.

Figure 14:
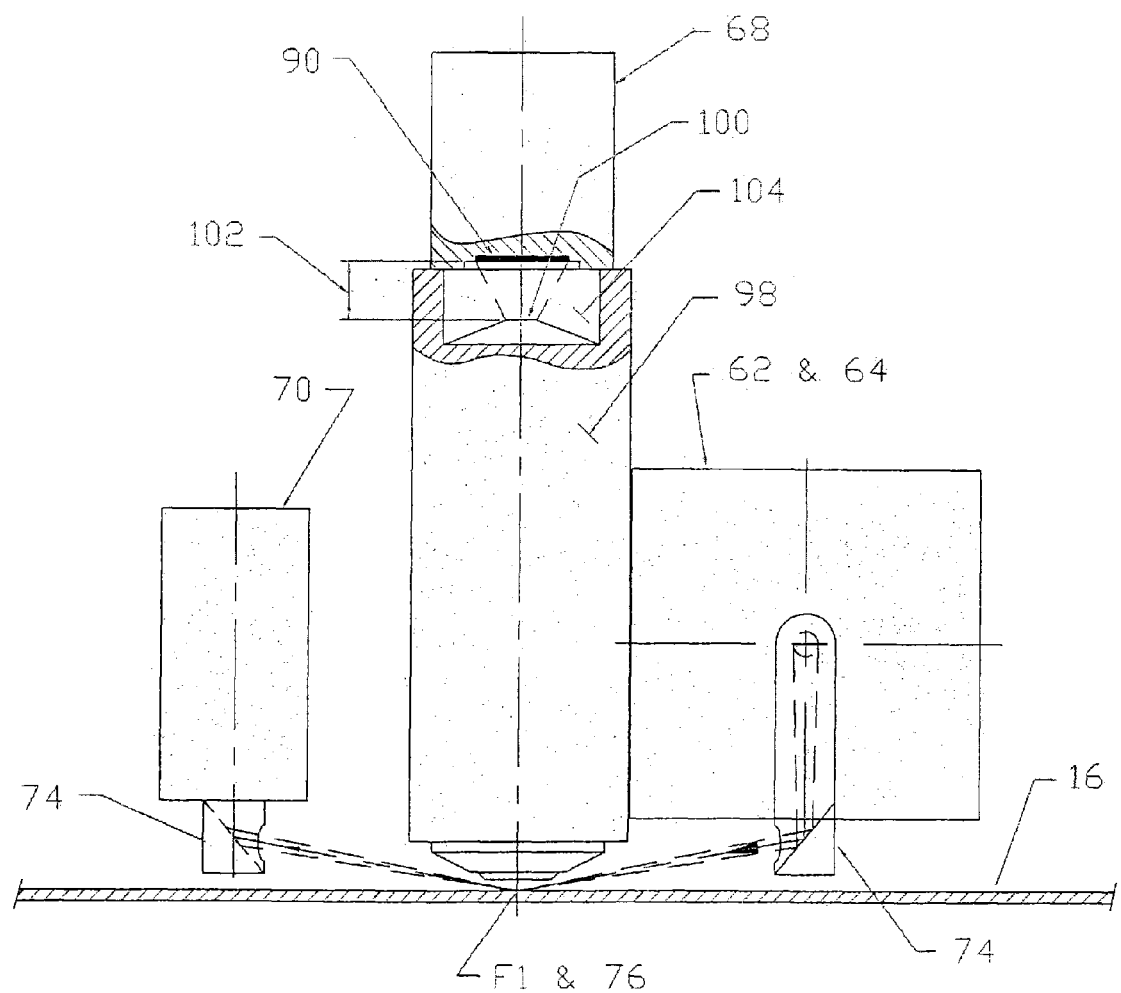
FIG. 14 is a side view of an alternate embodiment of the instrument group arrangement with a high numerical aperture infinity corrected lens substituted for the high numerical aperture highly elongate ellipsoidal reflector of the first embodiment.

FIG. 14 illustrates an alternate embodiment of instrument group 14 involving use of a high numerical aperture ($\geq 0.70$) infinity-corrected lens 98 in place of the ellipsoidal reflector 66 (see FIG. 10A). All other components of the system are as already described and are shown in correct relative size proportions to each other. Lens 98 has a preferable length to diameter ratio of $\geq 2.75:1$. The exit aperture 100 of the lens and ray dump cavity 104 are positioned relative to the sensitive face of detector 68 as previously described for the ellipsoidal reflector 66. If necessary, the lens system can have notches in it to pass the incident and reflected laser beams.

In the preferred embodiment, detector 68 (in FIGS. 10A and 14) is a miniature state-of-the-art ultra fast response photomultiplier tube (PMT) and ultra high-speed amplifier combination and is not further discussed herein. In an alternate embodiment of sensor 68, a solid state CCD (charged coupled device) camera can be mounted on a linear or rotary stage (remotely activated) with the PMT so both can move together between first and second positions where in a first position the PMT is disposed over the scattered light collector (ellipsoidal reflector 66 in FIG. 10A or lens 98 in FIG. 14) and a second position where the CCD camera is disposed over the scattered light collector. The CCD camera thus positioned allows visual inspection of the scattered light signature 75 (see FIGS. 11A and 11B) from a particular contaminant which can provide information about its characteristics. The CCD camera would only be used when the wafer rotation and instrument group arm are stopped and the wafer is positioned so that a particular contaminant is positioned under the scattered light collector by commands from an operator.

Figure 15B:
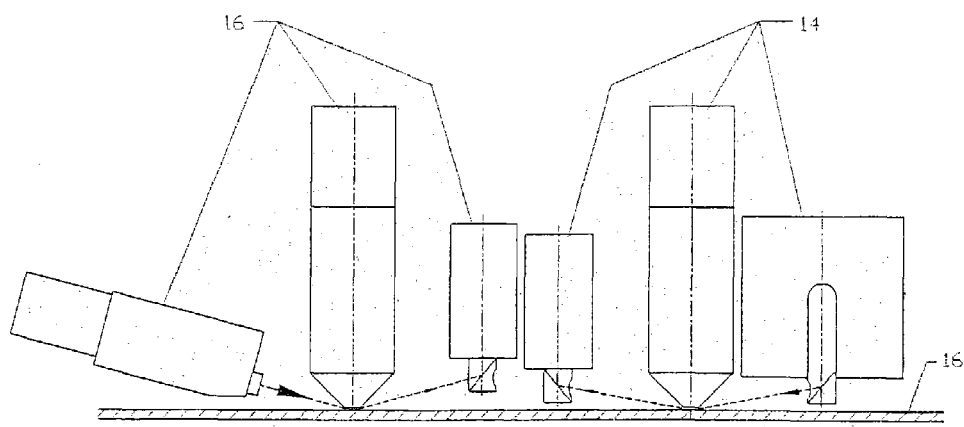
FIG. 15B is a view looking at the end of pivoting arm 24 in FIG. 15A to better show the arrangement of the two instrument groups.
Figure 15A:
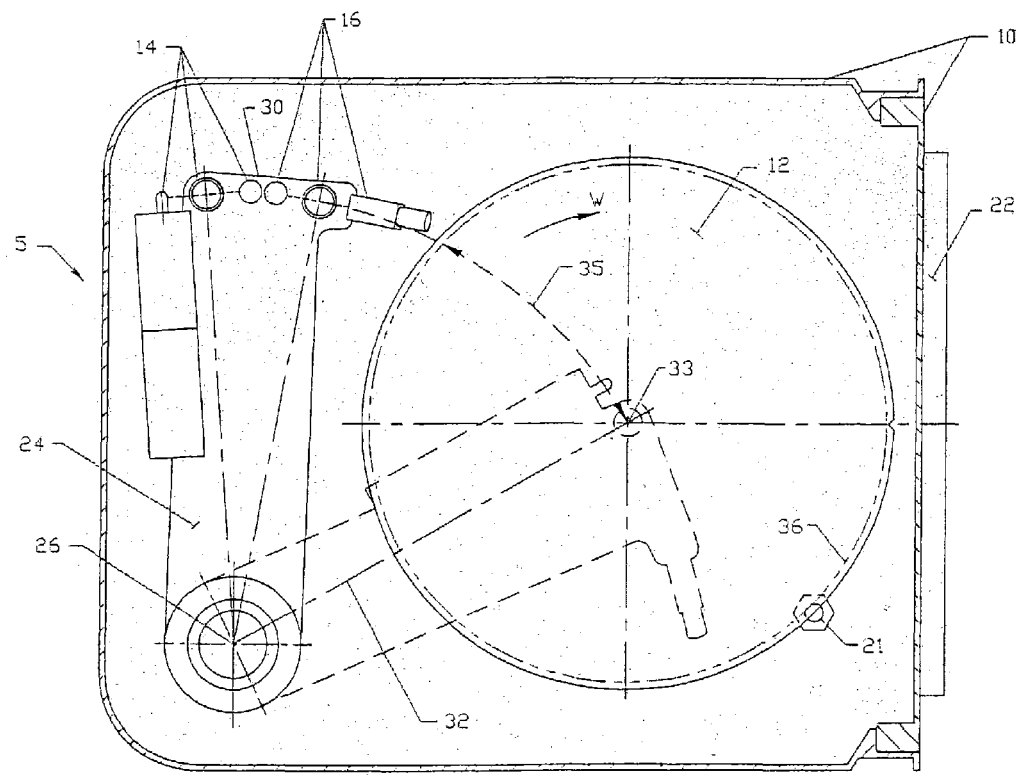
FIG. 15A is a top view of an alternate embodiment of the FIG. 1 apparatus with two instrument groups operating simultaneously, one in the $\leq 470$ nm and the other in the $\geq 700$ nm wavelength ranges, so as to illuminate contaminants from two opposite directions in a single scan pass.

FIG. 15A illustrates another alternate embodiment, similar to that illustrated in FIG. 1, wherein two instrument groups (14 and 16) are used. All elements are as defined in FIG. 1 except the configuration of pivoting arm 24 and instrument group 16. Instrument group 14 is comprised of laser/optics in the $\leq 470$ nm wavelength range while instrument group 16 is comprised of laser/optics in the $\geq 700$ nm wavelength range to take advantage of two optional wavelength ranges in one sweep of pivoting arm 24 to possibly enhance contaminant detection resolution. The two instrument groups are disposed apart on pivoting arm 24 as shown in FIG. 15B (view looking at the free end of arm 24 in FIG. 15A) so that each contaminant is successively illuminated from opposite sides as the instrument groups sweeps in arc 35. Both instrument groups take data only when they are individually between start scan circle 36 and stop scan point 33. No data is taken when pivoting arm 24 returns from position 32 to park position 30. Unlike the configuration of FIG. 3 this embodiment will not halve the scan time.

It follows that the "two opposite side illumination concept" of FIG. 15A can be extrapolated to configurations wherein both laser wavelengths are the same or wherein more than two lasers all at the same or different wavelengths are employed.

Having described and illustrated the principles of the invention in preferred and other embodiments thereof, it should be apparent that the invention can be modified in arrangement and detail without departing from such principles. We claim all modifications and variations coming within the spirit and scope of the following claims.

We claim:

1. A method for locating/sizing contaminants on a bare, highly polished, and planar surface of a dielectric or semiconductor material, comprising the steps of:

focusing a coherent beam of diffraction limited monochromatic P-polarized light from a solid-state (no gas plasma involved) light source and directed specifically at Brewster's angle (principal angle) to form a quasi-elliptical illuminated spot on the material surface which specularly reflects a circular minimal power beam from the surface of the material the cross-section of which has a dark (no-light) central band and two outer low light lobes;

causing a contaminant on the material surface to pass multiple times through the quasi-elliptical illuminated spot incident on the material surface so that the contaminant, on each pass through the illuminated spot, scatters the light in a quasi-hemispherical pattern; and disposing a high numerical aperture light collector, focused on the center of the quasi-elliptical illuminated spot, above and in close proximity to the material surface so as to redirect essentially all the light scattered (with effectively no secondary redirection) from the contaminant to a detector capable of converting the light collected to an electrical signal proportional to the light intensity.

2. The method of claim 1, wherein the high numerical aperture light collector, the detector, and all optics are optimized for the wavelength of the incident monochromatic light beam.

3. The method of claim 1, further including the step of disposing the light collector relative to the material surface so that effectively no reflected light, resulting from the incidence of the beam on the material surface is captured by the light collector.

4. The method of claim 1, wherein the high numerical aperture light collector is a highly elongate ellipsoidal reflector with an internal reflecting surface and an equivalent numerical aperture of $\geq 0.85$.

5. The method of claim 4, wherein the ellipsoidal reflector includes a major to minor axes ratio of at least 4.5:1, a reflective inner surface that extends 90–95% of the distance between the two focal points, and an ellipsoid minor diameter to entrance aperture diameter ratio of $\geq 3.1:1$.

6. The method of claim 4, further including disposing the ellipsoidal reflector relative to the material surface so that a line between focal points of the reflector is normal to the material surface.

7. The method of claim 4, further including positioning the ellipsoidal reflector relative to the incident P-polarized light beam and the specularly reflected light beam so that the beams pass between a bottom surface of the ellipsoidal reflector and the material surface with no interference.

8. The method of claim 4, wherein the ellipsoidal reflector includes first and second notches formed into the bottom surface of the ellipsoidal reflector, the first notch adapted to pass with no interference the incident P-polarized light beam there-through and the second notch adapted to pass with no interference the light beam specularly reflected from the material surface there-through.

9. The method of claim 1, wherein the high numerical aperture light collector is a refractive lens system with a numerical aperture of $\geq 0.7$.

10. The method of claim 9, wherein the refractive lens system is an infinity-corrected system with a numerical aperture of $\geq 0.7$.

11. The method of claim 10, wherein the refractive lens system has a length to diameter ratio of $\geq 2.75:1$.

12. The method of claim 9, further including disposing the refractive lens system relative to the material surface so that its optical axis is normal to the wafer surface.

13. The method of claim 9, further including positioning the refractive lens system relative to the incident P-polarized light beam and the specularly reflected light beam such that the beams pass between a bottom surface of the refractive lens system and the material surface with no interference.

14. The method of claim 9, wherein the refractive lens system includes first and second notches formed into the bottom surface of the refractive lens system, the first notch adapted to pass with no interference the P-polarized light beam there-through and the second notch adapted to pass with no interference the light specularly reflected from the material surface there-through.

15. The method of claim 1 further including disposing a beam dump to trap and fully dissipate the entire two-lobe beam that is specularly reflected from the material surface.

16. The method of claim 15, the beam dump including a low numerical aperture light collector and detector combination, the method further including collecting substantially all of the two lobe beam specularly reflected from the material surface, allowing the collected beam to be viewed on a remote display, and fully dissipating the collected beam.

17. The method of claim 16, wherein the detector includes a CCD camera, a linear (1D) light position detector, or a quadrant (2D) light position detector.

18. The method of claim 1, further including the steps of: grouping the light source, the high numerical aperture scattered light collector, and the detector together into an instrument group, mounting the instrument group on an arm, and moving the instrument group in unison within a plane above and parallel to the material surface.

19. The method of claim 18, further including rotating the material surface on a base about an axis of rotation perpendicular to the material surface and then simultaneously moving the instrument group within a plane that is above and parallel to the material surface from outside the periphery of the material surface to at least the axis of rotation of the material surface so that the quasi-elliptical spot can illuminate any desired area of the material surface.

20. The method of claim 19, wherein the instrument group is mounted on the free end of a pivot arm so that the quasi-elliptical spot moves in an arc to illuminate a desired area on the material surface in a spiral pattern due to the rotation of the material surface and the arc path of the instrument group arm above the material surface.

21. The method of claim 19, further including mounting the instrument group on a free end of non-pivoting arm and moving the quasi-elliptical spot in a straight line to illuminate a desired area on the material surface in a spiral pattern as the material surface is rotated under the instrument group arm.

22. The method of claim 18, further including disposing and controlling two or more instrument groups separately on an arm to reduce the scan time by a factor of two or more, each instrument group including a light source and a collector/detector assembly, and illuminating a same side of a contaminant with the light source of each instrument group.

23. The method of claim 22, further including disposing the instrument groups apart so that the illuminated spot from each group follows a portion of a continuous arc path on the material surface and the plane of each incident light beam and its normal to the material surface are tangent to the arc path.

24. The method of claim 18, further including arranging and controlling two or more instrument groups separately on an arm so as to illuminate each contaminant from two or more sides; each instrument group comprised of a light source and a collector/detector assembly and with any two light sources illuminating generally opposite sides of a contaminant.

25. The method of claim 24, further including disposing the instrument groups apart so that the illuminated spot from each group follows the same arc path and arc length on the material surface and the plane of each incident light beam and its normal to the material surface is tangent to the arc path.

26. The method of claim 18, further including moving the material surface in a straight line and simultaneously moving the instrument group(s) as a single unit in a straight line perpendicular to the straight line motion of the material surface, from outside the periphery of the material piece so the quasi-elliptical spot(s) can illuminate any desired area of the material surface in a rectangular two dimensional pattern.

27. The method of claim 18 further including moving the instrument group and the material surface so as to position the light collector and incident illuminated spot over a desired contaminant and statically capturing a scattered light pattern from the desired contaminant on a remote display.

28. The method of claim 18, further including disposing a beam dump to trap and fully dissipate the entire two-lobe beam that is specularly reflected from the material surface.

29. The method of claim 1, further including the step of disposing a scattered ray dump about the sensitive face of the detector and the exit aperture of the light collector.

30. The method of claim 1, wherein the contaminant scattered light collector/light-dump/detector assembly is configured so that the scattered light rays (photons) pass only one time through the assembly.

31. The method of claim 1, wherein a detector is disposed to provide an electrical signal from a datum on the material surface.

32. The method of claim 1, further including associating time and the detector signals with a fixed location on the material surface.

33. The method of claim 1, further including storing, processing, and comparing the multiple electrical signals from the detector created by each contaminant to a calibration curve relating processed signal magnitude to that from standardized (size, shape, and material) contaminants and to a fixed datum location on the material surface.

34. An apparatus for locating/sizing contaminants on a bare, highly polished, and planar surface of a dielectric or semiconductor material comprising:

- means for directing a focused coherent diffraction limited beam of monochromatic P-polarized light from a solid-state (no gas plasma involved) light source and specifically disposed at Brewster's angle (principal angle) to form a quasi-elliptical illuminated spot on the material surface that specularly reflects a circular minimal power beam from the material surface the cross-section of which has a dark (no-light) central band and two outer low light lobes; the center of said illuminated spot coincident with the focal point of the beam on the beam optical axis and on the material surface;
- a high numerical aperture light collector disposed above and in close proximity with the material surface and focused on the center of the quasi-elliptical illuminated spot on the material surface to maximize capture of quasi-hemispherically scattered light from a contaminant illuminated by the light beam incident on the material surface; and
- a detector disposed near the exit aperture of the light collector opposite the material surface for generating a signal indicative of the intensity of the scattered light captured by and redirected through the light collector to the detector.

35. The apparatus of claim 34, wherein the high numerical aperture light collector, the detector, and all optics are optimized for the wavelength of the incident monochromatic light beam.

36. The apparatus of claim 34, further including the step of disposing the light collector relative to the material surface so that effectively no reflected light, resulting from the incidence of the beam on the material surface, is captured by the light collector.

37. The apparatus of claim 34, wherein the high numerical aperture light collector is a highly elongate ellipsoidal reflector with an internal reflecting surface and an equivalent numerical aperture of $\geq 0.85$.

38. The apparatus of claim 37, wherein the ellipsoidal reflector includes a major to minor axes ratio of at least 4.5:1, a reflective inner surface that extends 90–95% of the distance between the two focal points, and an ellipsoid minor diameter to entrance aperture diameter ratio of $\geq 3.1:1$.

39. The apparatus of claim 37, wherein the ellipsoidal reflector is disposed relative to the material surface so that a line between focal points of the reflector is normal to the material surface.

40. The apparatus of claim 37, wherein the ellipsoidal reflector is positioned relative to the incident P-polarized light beam and the specularly reflected light beam so that the beams pass between a bottom surface of the ellipsoidal reflector and the material surface with no interference.

41. The apparatus of claim 37, wherein the ellipsoidal reflector includes first and second notches formed into the bottom surface of the ellipsoidal reflector, the first notch adapted to pass with no interference the incident P-polarized light beam there-through and the second notch adapted to pass with no interference the light beam specularly reflected from the material surface there-through.

42. The apparatus of claim 34, wherein the high numerical aperture light collector is a refractive lens system with a numerical aperture of $\geq 0.7$.

43. The apparatus of claim 42, wherein the refractive lens system is an infinity-corrected system with a numerical aperture of $\geq 0.7$.

44. The apparatus of claim 43, wherein the refractive lens system has a length to diameter ratio of $\geq 2.75:1$.

45. The apparatus of claim 42, wherein the refractive lens system is disposed relative to the material surface so that its optical axis is normal to the wafer surface.

46. The apparatus of claim 42, wherein the refractive lens system is positioned relative to the incident P-polarized light beam and the specularly reflected light beam such that the beams pass between a bottom surface of the refractive lens system and the material surface with no interference.

47. The apparatus of claim 42, wherein the refractive lens system includes first and second notches formed into the bottom surface of the refractive lens system, the first notch adapted to pass with no interference the P-polarized light beam there-through and the second notch adapted to pass with no interference the light specularly reflected from the material surface there-through.

48. The apparatus of claim 34 further including a beam dump arranged and configured to trap and fully dissipate the entire two-lobe beam that is specularly reflected from the material surface.

49. The apparatus of claim 48, wherein the beam dump includes a low numerical aperture light collector and detector combination to collect all of the two lobe beam specularly reflected from the material surface, allow it to be viewed on a remote display, and to fully dissipate it.

50. The apparatus of claim 49, wherein the detector is a CCD camera, a linear (1D) light position detector, or a quadrant (2D) light position detector.

51. The apparatus of claim 34, wherein the light source, the high numerical aperture scattered light collector, and the detector together are grouped into an instrument group, mounted on an arm, and arranged and configured for movement in unison within a plane above and parallel to the material surface.

52. The apparatus of claim 51, wherein the material surface is arranged and configured for rotation on a base about an axis of rotation perpendicular to the material surface, said instrument group moveable within a plane that is above and parallel to the material surface from outside the periphery of the material surface to at least the axis of rotation of the material surface so that the quasi-elliptical spot can illuminate any desired area of the material surface.

53. The apparatus of claim 52, wherein the instrument group is mounted on the free end of a pivot arm so that the quasi-elliptical spot moves in an arc to illuminate a desired area on the material surface in a spiral pattern due to the rotation of the material surface and the arc path of the instrument group arm above the material surface.

54. The apparatus of claim 53, further including an ultra-low vibration and speed-controlled electric motor coupled to the pivot arm.

55. The apparatus of claim 52, wherein the instrument group is mounted on the free end of non-pivoting arm so that the quasi-elliptical spot is capable of moving in a straight line to illuminate a desired area on the material surface in a spiral pattern due to the rotation of the material surface and the straight line path of the instrument group arm above the material surface.

56. The apparatus of claim 55, further including an ultra-low vibration and speed-controlled electric motor driven linear stage coupled to the non-pivoting arm and arranged and configured to move the instrument group non-pivoting arm in a straight line.

57. The apparatus of claim 52, further including an ultra-low vibration and speed-controlled electric motor arranged and configured to move the instrument group non-pivoting arm in a straight line, and further including a vacuum chuck and non-contact vacuum line coupling, wherein the vacuum chuck dimensions allow a SEMI (Semiconductor Equipment and Materials Industry) standard robot end-effector to place, center, and remove the material piece.

58. The apparatus of claim 51, further including disposing and controlling two or more instrument groups separately on an arm to reduce the scan time by two or more; each instrument group comprised of a light source and a collector/detector assembly and with the light sources illuminating generally the same side of a contaminant.

59. The apparatus of claim 58, further including disposing the instrument groups apart so that the illuminated spot from each group follows a portion of a continuous arc path on the material surface and the plane of each incident light beam and its normal to the material surface is tangent to the arc path.

60. The apparatus of claim 51, further including arranging and controlling two or more instrument groups separately on an arm so as to illuminate each contaminant from two or more sides; each instrument group comprised of a light source and a collector/detector assembly and with any two light sources illuminating generally opposite sides of a contaminant.

61. The apparatus of claim 60, further including disposing the instrument groups apart so that the illuminated spot from each group follows the same arc path and arc length on the material surface and the plane of each incident light beam and its normal to the material surface is tangent to the arc path.

62. The apparatus of claim 51, the material surface being moveable in a straight line and the instrument group simultaneously moveable as a single unit in a straight line perpendicular to the straight line motion of the material surface from outside the periphery of the material piece so the quasi-elliptical spot(s) can illuminate any desired area of the material surface in a rectangular two dimensional pattern.

63. The apparatus of claim 62 further including ultra-low vibration and speed-controlled electric motor drive linear stages for moving the instrument group arm in a straight line relative to the material surface.

64. The apparatus of claim 51 further including a capability to jog the instrument group(s) as a single unit and the movement of the material surface so as to position a particular light collector and incident illuminated spot over any desired contaminant and statically capture its scattered light pattern on a remote display.

65. The apparatus of claim 51, further including a beam dump as part of the instrument group that is arranged and configured to trap and fully dissipate the entire two-lobe beam that is specularly reflected from the material surface.

66. The apparatus of claim 34, wherein all of the components are packaged in an air-tight sealable container with a sealable door to allow appropriate insertion of a material piece into the container and that is sized to fit a SEMI (Semiconductor Equipment and Materials Institute) standard FOUP loadport for 300 mm diameter wafers.

67. The apparatus of claim 66, wherein the container is filled with a gas other than ambient air.

68. The apparatus of claim 66, wherein the container is evacuated.

69. The apparatus of claim 66, the container including strategically placed baffles and laminar flow surface shapes for suppressing gas turbulence inside the container caused by spinning material surface drag.

70. The apparatus of claim 66, further including means for suppressing internal and external vibrations that could distort an output signal from the scattered light detector.

71. The apparatus of claim 34, further including means for tracking the material surface to effectively eliminate distortion of the output signal from the scattered light detector due to material surface dimensional tolerances (warp, waviness, etc).

72. The apparatus of claim 34 wherein the light source is a coherent and monochromatic laser that (1) is small ($\leq$[5 in. L×3 in. W×1.25 in. H]), (2) is light-weight ($\leq$0.5 lb.), (3) is solid-state (no gas plasma involved), (4) is thermoelectrically cooled, (5) operates only in a continuous wave (CW) TEMoo mode, (6) has a mode quality $M^2 \leq 1.1$, (7) has a capability to adjust beam power from its maximum through a computer, (8) has a beam polarization ratio $\geq$100:1, (9) can be focused (with appropriate optics) to a diffraction limited spot with a circular cross-section, a Gaussian irradiance profile centered about the optical axis and a diameter in the range of 8 to 12 microns, and (10) can be operated at full power for at least 10,000 hours.

73. The apparatus of claim 72, wherein the laser operates at a single wavelength within the ranges $\leq$470 nm or $\geq$700 nm.

74. The apparatus of claim 72, wherein the laser operates at a single wavelength within the ranges >470 nm and <700 nm.

75. The apparatus of claim 34, further including a scattered ray dump disposed about a sensitive face of the detector and the exit aperture of the light collector.

76. The apparatus of claim 34, further including a CCD camera mounted on a linear or rotary stage with the scattered light sensor where both can move together between first and second positions where in a first position the scattered light detector is disposed over the scattered light collector and in a second position where the CCD camera is disposed over the scattered light collector to allow visual inspection of the scattered light signature from a particular contaminant on a remote monitor.

77. The apparatus of claim 34, wherein the contaminant scattered light collector/light-dump/detector assembly is configured so that the scattered light rays (photons) pass only one time through the assembly.

78. The apparatus of claim 34, wherein a detector is disposed to provide an electrical signal from a datum on the material surface.

79. The apparatus of claim 34, further including means for associating time and the detector signals with a fixed location on the material surface.

80. The apparatus of claim 34, further including means for storing, processing, and comparing the multiple electrical signals from the detector created by each contaminant to a calibration curve relating processed signal magnitude to that from standardized (size, shape, and material) contaminants and to a fixed datum location on the material surface.

81. The apparatus of claim 34, wherein the light source/optics, the scattered light collector/detector subassembly, and a optional reflected light beam dump are disposed on a pivot or linear motion arm/motor-drive subsystem, the vacuum chuck subsystem with its integrated motion-drive/vacuum-coupling subsystems, a material surface datum detector, and support electronics are integrated into a first portable module that is the approximate size of a SEMI standard 300 mm FOUP that can lock to a SEMI standard load-port or other through-the-wall clean-room interface and that is connected via a portable umbilical to a second portable module containing self-contained power, vacuum, data capture/processing/control/data-display, and docking/undocking subsystems for the first module.

82. The apparatus of claim 81 wherein the first and second portable modules are integrated onto a SEMI standard load-port panel, the self contained power/vacuum supplies are obtained from sources external to the overall assembly, and the umbilical and docking/undocking of the first/second portable modules are eliminated.

83. The apparatus of claim 82 wherein the data capture/processing/control/data-display subsystems are located remote from the overall assembly in a central facility control center and connected via hard wire or wireless means.

* * * * *